United States Patent
Sung et al.

(10) Patent No.: US 7,323,328 B2
(45) Date of Patent: Jan. 29, 2008

(54) **OBLIGATELY SYMBIOTIC THERMOPHILE *SYMBIOBACTERIUM TOEBII* SC-1 PRODUCING THERMOSTABLE L-TYROSINE PHENOL-LYASE AND L-TRYPTOPHAN INDOLE-LYASE**

(75) Inventors: Moon-Hee Sung, Daejeon-si (KR); Seung-Goo Lee, Daejeon-si (KR); Sung-Keun Rhee, Daejeon-si (KR); Seung-Pyo Hong, Daejeon-si (KR); Dae-Joong Kang, Seoul-si (KR); Su-Mi Kim, Daejeon-si (KR); Chul-Joong Kim, Daejeon-si (KR); Jin-Woo Bae, Daejeon (KR); Che Ok Jeon, Ithaca, NY (US); Joong-Jae Kim, Daegu (KR); Kwang Kim, Daejeon (KR); Jae Jun Song, DaeJeon (KR)

(73) Assignee: Korea Research Institute of Bioscience and Biotechnology, Taejon-si (KR)

( * ) Notice: Subject to any disclaimer, the term of this patent is extended or adjusted under 35 U.S.C. 154(b) by 251 days.

(21) Appl. No.: 11/186,559

(22) Filed: Jul. 21, 2005

(65) Prior Publication Data
US 2005/0255090 A1   Nov. 17, 2005

Related U.S. Application Data

(62) Division of application No. 10/220,174, filed as application No. PCT/KR00/00764 on Jul. 14, 2000, now Pat. No. 6,967,087.

(30) Foreign Application Priority Data
Mar. 2, 2000   (KR) ............................... 2000-10508

(51) Int. Cl.
*C12N 1/20* (2006.01)
*C12N 9/88* (2006.01)
*C12P 39/00* (2006.01)

(52) U.S. Cl. ...................... 435/252.1; 435/37; 435/39; 435/42; 435/232; 435/252.3; 435/252.31; 435/252.5; 435/253.6; 435/254.4; 424/93.4

(58) Field of Classification Search ............. 435/253.6, 435/37, 39, 232, 252.3, 252.31, 252.5, 252.4
See application file for complete search history.

(56) References Cited

U.S. PATENT DOCUMENTS

| | | | | | |
|---|---|---|---|---|---|
| 4,234,691 | A | * | 11/1980 | Kusakabe et al. | 435/191 |
| 5,776,740 | A | * | 7/1998 | Hatakeyama et al. | 435/108 |
| 5,916,781 | A | * | 6/1999 | Yamamoto et al. | 435/108 |
| 6,967,087 | B1 | * | 11/2005 | Sung et al. | 435/42 |

FOREIGN PATENT DOCUMENTS

| | | |
|---|---|---|
| JP | 5056779 A2 | 3/1993 |
| JP | 11042097 A2 | 2/1999 |

OTHER PUBLICATIONS

Seung-Goo Lee et al., "Thermostable Tyrosine Phenol-Lyase of Symbiobacterium sp. SC-1: Gene Cloning, Sequence Determination, and Overproduction in *Escherichia coli*," Protein Expression and Purification 11:263-270 (1997).
Michiyo Ohno et al., "Establishing the Independent Culture of a Strictly Symbiotic Bacterium *Symbiobacterium thermophilum* from Its Supporting Bacillus Strain," Biosci. Biotechnol. Biochem., 63(6):1083-1090 (1999).

* cited by examiner

*Primary Examiner*—Herbert J. Lilling
(74) *Attorney, Agent, or Firm*—Gates & Cooper LLP (57) ABSTRACT

The present invention relates to a novel obligately symbiotic thermophile *Symbiobacterium toebii* SC-1 (Accession NO: KCTC 0685BP), and a thermostable L-tyrosine phenol-lyase and L-tryptophan indole-lyase produced by *Symbiobacterium toebii* SC-1. The present invention also relates to a pure culture method of *Symbiobacterium toebii* SC-1, a method of growth measurement for *Symbiobacterium toebii* SC-1 and its relative symbiotic bacteria showing low-growth yield using nitrate respiration, and a screening method of relative symbiotic strains of *Symbiobacterium toebii* SC-1 from the environment using a specific antibody to it. Therefore, the thermostable L-tyrosine phenol-lyase and L-tryptophan indole-lyase produced by *Symbiobacterium toebii* SC-1 in this invention can provide more stable catalysts in enzymatic biotransformation processes which enzymatically produce valuable medico-amino acids 3,4-dehydroxy-L-phenylalanine (L-DOPA) and L-tryptophan.

4 Claims, 6 Drawing Sheets

OBLIGATELY SYMBIOTIC THERMOPHILE *SYMBIOBACTERIUM TOEBII* SC-1 PRODUCING THERMOSTABLE L-TYROSINE PHENOL-LYASE AND L-TRYPTOPHAN INDOLE-LYASE

This application is a divisional of U.S. patent application Ser. No. 10/220,174, filed Aug. 28, 2002, now U.S. Pat. No. 6,967,087, issued Nov. 22, 2005, which was filed as PCT application number KR00/00764 on Jul. 14, 2000, and claims benefit of Korean Patent application number 2000/10508, filed Mar. 2, 2000, the entire contents of each of which is incorporated herein by reference.

FIELD OF THE INVENTION

The present invention relates to a novel obligately symbiotic thermophile producing thermostable L-tyrosine phenol-lyase and L-tryptophan indole-lyase and relates to a method for screening the relative bacteria of the novel obligately symbiotic thermophile.

Particularly, the present invention relates to a novel obligately symbiotic thermophile, *Symbiobacterium toebii* SC-1 isolated from a high-temperature environment; to two enzymes, thermostable L-tyrosine phenol-lyase and L-tryptophan indole-lyase, produced by *Symbiobacterium toebii* SC-1 which is cultivated by a pure culture method without mixed culture of its symbiotic partner, *Bacillus* sp. SK-1; to a method for the growth measurement of *Symbiobacterium toebii* SC-1 which shows a low-growth yield; and to a method for screening its relative symbiotic bacteria using a specific antibody to the *Symbiobacterium toebii* SC-1.

The thermostable L-tyrosine phenol-lyase and L-tryptophan indole-lyase produced by *Symbiobacterium toebii* SC-1 of this present invention can be used in enzymatic biotransformation processes which enzymatically produce valuable medico-amino acids 3,4-dehydroxy-L-phenylalanine (hereinafter, as referred as "L-DOPA") and L-tryptophan.

BACKGROUND

Generally, L-tyrosine phenol-lyase is a ubiquitous enzyme produced by *Erwinia* sp., *Escherichia* sp. and Gram-negative intestinal bacteria which are cultivated in medium containing tyrosine as an inducer.

L-tyrosine phenol-lyase catalyzes the α,β-elimination reaction which hydrolyzes tyrosine into phenol, pyruvate and ammonia. It also catalyzes the tyrosine synthesis reaction which is reversible to the α,β-elimination reaction (see Scheme 1). When catechol, pyruvate and ammonia are provided, L-tyrosine phenol-lyase synthesizes a valuable amino acid, L-DOPA.

<Scheme 1>

On the other hand, L-tryptophan indole-lyase catalyzes the α,β-elimination reaction which hydrolyzes L-tryptophan into indole, pyruvate and ammonia. However, if ammonium is present at a high concentration in the medium, L-tryptophan is synthesized from indole and pyruvate by reverse α,β-elimination (synthesis) reaction (see Scheme 2).

<Scheme 2>

-continued

Tryptophan

+ $H_2O$

As mentioned above, L-tyrosine phenol-lyase and L-tryptophan indole-lyase are induced by L-tyrosine and L-tryptophan as inducers in the medium, respectively.

It has been reported that the valuable medico-amino acid, L-DOPA is effective in treating Parkinson's disease. Generally, L-DOPA is produced by enzymatic reaction using L-tyrosine phenol-lyase. An enzymatic biotransformation process of L-DOPA production generally uses an enzyme derived from mesophile. The enzyme stability in the enzymatic biotransformation process of L-DOPA production plays a key role in increasing the productivity and production rate. However, the enzyme derived from mesophile has low-stability to heat, so it is easily denatured. In addition, because it is very unstable in extreme conditions of processes using solvents, high pressure, extreme acidity or alkalinity, the productivity and production rate of the enzymatic biotransformation process is decreased.

To overcome these problems of enzymes derived from mesophile, we made an effort to develop technology using an enzyme derived from a thermophile in an enzymatic biotransformation process. Generally, a thermophile adapted to a high-temperature environment has thermostable enzymes stable to heat. Since the thermostable enzymes have a stability to solvents, a high concentration of hydrogen ions or chemical detergents as well as a stability to heat, we propose the possible industrial use of thermostable enzymes in an enzymatic biotransformation process (KR Patent No 0229284).

To discover a novel thermostable L-tyrosine phenol-lyase and L-tryptophan indole-lyase that could be used for the above enzymatic biotransformation process of L-DOPA and L-tryptophan production, the present inventors have developed a pure culture method of symbiotic bacteria. Using the pure culture method, these inventors have identified a novel obligately thermophile *Symbiobacterium toebii* SC-1 showing a high activity of thermostable L-tyrosine phenol-lyase and L-tryptophan indole-lyase.

In addition, the present inventors have developed a method of growth measurement for *Symbiobacterium toebii* SC-1 showing a low-growth yield, and a screening method of its relative symbiotic bacteria using a specific antibody to it.

SUMMARY OF THE INVENTION

It is an objective of this invention to provide a novel obligately symbiotic thermophile showing a high enzyme activity of thermostable L-tyrosine phenol-lyase and L-tryptophan indole-lyase.

It is a further objective of this invention to provide a screening method for relative symbiotic bacteria of the novel obligately symbiotic thermophile from the environment using a specific antibody.

In accordance with the present invention, the foregoing objectives and advantages are readily obtained.

The present invention provides a novel obligately symbiotic thermophile, *Symbiobacterium toebii* SC-1.

This invention also provides thermostable L-tyrosine phenol-lyase and L-tryptophan indole-lyase produced by the novel *Symbiobacterium toebii* SC-1.

This invention provides an pure culture method for obtaining the novel *Symbiobacterium toebii* SC-1.

In addition, this invention provides a method for growth measurement of the novel *Symbiobacterium toebii* SC-1 and its relative bacteria and a screening method of its relative symbiotic bacteria from the environment using a specific antibody to *Symbiobacterium toebii* SC-1.

Further features of the present invention will appear hereinafter.

BRIEF DESCRIPTION OF THE DRAWINGS

a: *Symbiobacterium toebii* SC-1.

b: *Bacillus* sp. SK-1.

a: optimal growth temperature.

b: optimal pH.

-▽-: the decrement of nitrate (mM).

-○-: the increment of nitrite (mM).

DETAILED DESCRIPTION OF PREFERRED EMBODIMENTS

Hereinafter, the present invention is described in detail.

The present invention presents the novel obligately symbiotic thermophile *Symbiobacterium toebii* SC-1 isolated from compost yards in Korea. It is confirmed that *Symbiobacterium toebii* SC-1 has obligate commensalism with a thermophilic *Bacillus* sp. SK-1 (Accession NO: KCTC 0306BP).

Isolation, a pure culture method, morphological and physiological characteristics of *Symbiobacterium toebii* SC-1 of this invention are as follows.

1) Isolation of *Symbiobacterium toebii* SC-1

The present inventors detected two types of thermophilic bacteria in the enrichment culture showing L-tyrosine phenol-lyase activity. Various compost samples were inoculated to the enrichment medium containing L-tyrosine. They are novel Gram-negative thermophile, *Symbiobacterium toebii* SC-1 having thermostable L-tyrosine phenol-lyase activity and an endospore forming Gram-positive bacteria, thermophilic *Bacillus* sp. SK-1 and they have obligate commensalism with each other (see FIG. 1). The thermostable L-tyrosine phenol-lyase activity of *Symbiobacterium toebii* SC-1 is easily measured by detecting phenol in the culture medium with 4-aminoantipyrine.

By using this color development method, it was certain that an enrichment culture showing an intense red color contains novel thermophilic bacteria producing L-tyrosine phenol-lyase.

2) Pure Culture of *Symbiobacterium toebii* SC-1

Generally, it is impossible to independently cultivate thermophilic symbiotic bacteria without their symbiotic partner. In addition, only a small fraction of the bacterial communities can be cultivated into visible colony types by current technologies (Lee S. Y., et al., *Appl. Environ. Microbiol.*, 62, 3787-3797, 1996; Ward D. M., et al., *Microbiol. Mol. Biol. Rev.*, 62, 1353-1370, 1998) because of their interaction with other organisms (e.g., in symbiotic relationships) as well as the ability to reproduce real micro-environmental niches. For example, *Methanobacterium* sp. strains producing methanol from ethanol (Bryant et al., *Archiv. Fur. Microbiologie.*, 50, 20-31, 1967) and 2 types of *Pseudomonas* sp. strains degrading polyvinylalchol (Shimao et al., *Agric. Biol. Chem.*, 48, 2873-2876, 1984) can be grown in only mixed cultures with their symbiotic partners. On the other hand, in parasitic interactions, bacterial parasites need essential growth factors from their host for their growth. It is reported that *Bedellovibrio* requires lysis of a Gram-negative bacterial host for its growth (Rudy E. G., *The Procaryotes*, 3400-3415, 1992).

The present inventors have identified a new obligately symbiotic thermophile *Symbiobacterium toebii* SC-1 during the screening of thermostable L-tyrosine phenol-lyase-producing thermophiles as described above. However, since *Symbiobacterium toebii* SC-1 obligately requires its symbiotic partner *Bacillus* sp. SK-1 to obtain essential growth factors, the present inventors could not separate *Symbiobacterium toebii* SC-1 from *Bacillus* sp. SK-1 and get a single colony of *Symbiobacterium toebii* SC-1.

Therefore, these inventors have developed a pure culture method using a modified basal medium (MBM) to isolate a single colony of *Symbiobacterium toebii* SC-1 from the mixed culture of *Symbiobacterium toebii* SC-1 and *Bacillus* sp. SK-1 and cultivate *Symbiobacterium toebii* SC-1 independently. These inventors developed an MBM containing crude extract and a culture supernatant of its symbiotic partner *Bacillus* sp. SK-1 as growth factors.

As a result, these inventors have isolated a single colony of a *Symbiobacterium toebii* SC-1 from the mixed culture of *Symbiobacterium toebii* SC-1 and *Bacillus* sp. SK-1 by the pure culture method using the MBM under anoxic conditions.

Therefore, the pure culture method using the MBM containing crude extract and culture supernatant of its symbiotic partner in this invention can be useful to independently cultivate the novel *Symbiobacterium toebii* SC-1 and its relative symbiotic bacteria.

3) Characteristics of *Symbiobacterium toebii* SC-1

Figure 2:
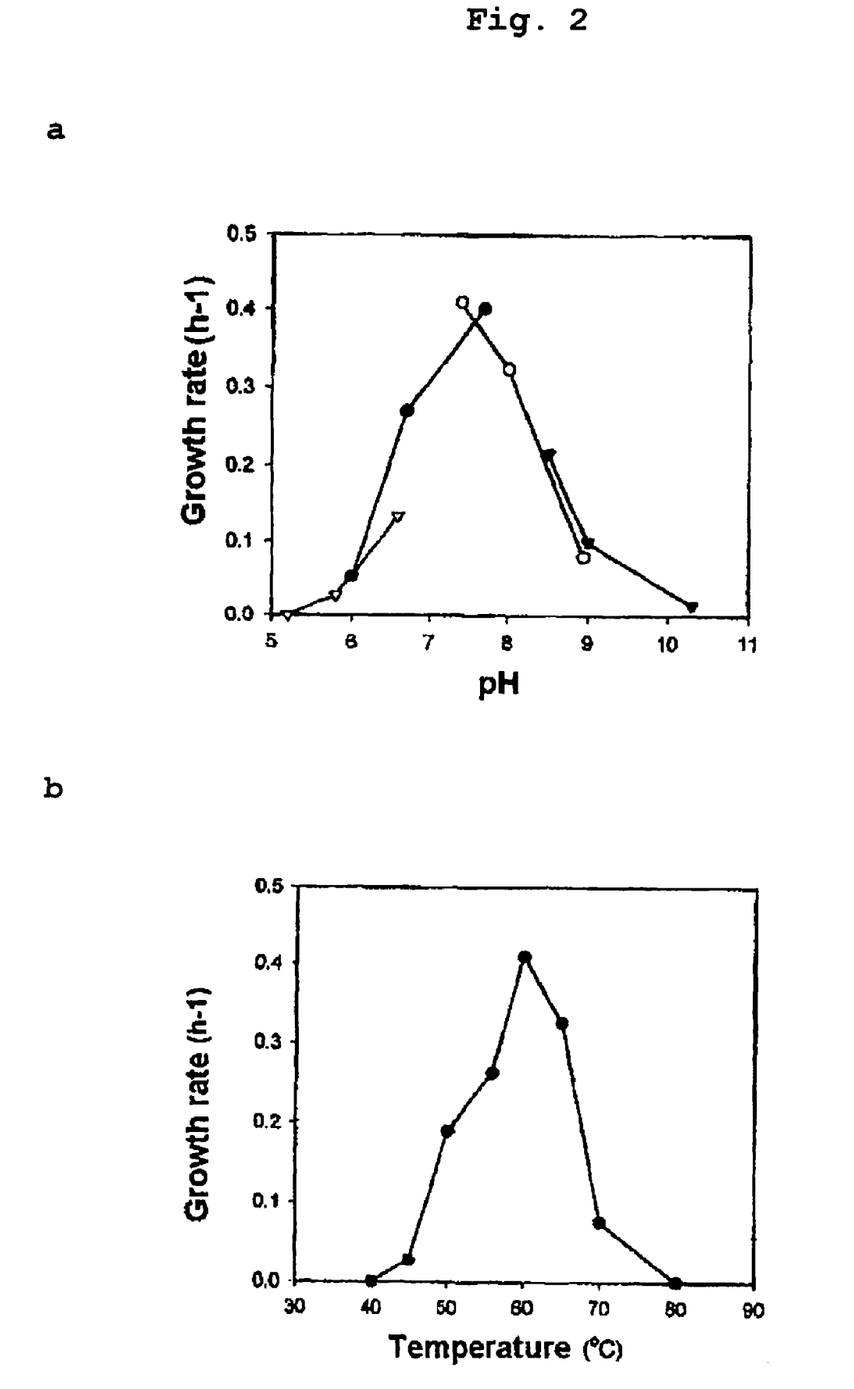
FIG. 2 shows the optimal growth temperature and pH of the novel *Symbiobacterium toebii* SC-1.

The optimal temperature and pH for growth of *Symbiobacterium toebii* SC-1 are about 60° C. and pH 7 to 8 (see FIG. 2). As a Gram-negative bacterium, *Symbiobacterium toebii* SC-1 is a novel symbiotic thermophile, but is not yet registered in the Bergey's Manual of Systematic Bacteriology.

As a result of phylogenetic analysis using 16s rRNA, *Symbiobacterium toebii* SC-1 shows a high similarity with a group of *Bacillus-Clostridium* which has the characteristics of endospore formation, anaerobic growth and thermostability.

On the basis of this, the inventors designated the novel symbiotic thermophile producing thermostable L-tyrosine phenol-lyase and L-tryptophan indole-lyase as *Symbiobacterium toebii* SC-1, and deposited it in the Korean Collection for Type Cultures (KCTC) at Korea Research Institute of Bioscience and Biotechnology (KRIBB) on Oct. 29, 1999 (Accession NO: KCTC 0685BP).

This invention also produces a thermostable L-tyrosine phenol-lyase and L-tryptophan indole-lyase.

To measure the enzyme activities of the thermostable L-tyrosine phenol-lyase and L-tryptophan indole-lyase produced by the novel symbiotic thermophile *Symbiobacterium toebii* SC-1, these inventors inoculated *Symbiobacterium toebii* SC-1 into liquid modified basal medium (MBM) and incubated it under anaerobic conditions with nitrates. Then they centrifuged the culture medium to separate cell pastes, and sonicated the cells to obtain a crude extract. Enzyme activities of thermostable L-tyrosine phenol-lyase and L-tryptophan indole-lyase produced by *Symbiobacterium toebii* SC-1 were measured using the crude extracts.

Particularly, the crude extract was mixed with Tris-HCl buffer and L-tyrosine or L-tryptophan as a substrate of L-tyrosine phenol-lyase or L-tryptophan indole-lyase, respectively. Pyruvate is produced during the enzyme reaction in the mixtures of crude extract with its respective substrate. The inventors could measure the enzyme activity by determining the amount of pyruvate produced.

As a result, it was confirmed that the novel symbiotic thermophile *Symbiobacterium toebii* SC-1 in this invention produces the thermostable L-tyrosine phenol-lyase and L-tryptophan indole-lyase and these enzymes have activities producing pyruvate from L-tyrosine or L-tryptophan, respectively.

Therefore, the thermostable L-tyrosine phenol-lyase and L-tryptophan indole-lyase produced by *Symbiobacterium toebii* SC-1 in this invention are very stable biocatalysts in the enzymatic biotransformation process that produces L-DOPA from catechol, pyruvate and ammonia, and L-tryptophan from indole, pyruvate and ammonia.

In addition, the present invention provides a method for measuring the growth of *Symbiobacterium toebii* SC-1 and its relative symbiotic bacteria showing a low-growth yield.

Since *Symbiobacterium* sp. strains are bacteria showing a very low final growth, it is impossible to represent their growth by measuring their absorbances at $OD_{600}$ using spectrophotometer but also by counting the number of micro-colonies.

So, these inventors used a nitrate reduction reaction under anaerobic conditions to determine the growth of *Symbiobacterium toebii* SC-1. The *Symbiobacterium toebii* SC-1 performs nitrate reduction under anaerobic growth conditions. *Symbiobacterium toebii* SC-1 uses nitrate as an electron acceptor and reduces nitrate into nitrite. It produces ATP using redox potential generated from nitrate reduction and uses ATP for its growth.

As mentioned above, because the growth of *Symbiobacterium toebii* SC-1 using nitrate reduction coincides with accumulation of nitrite, its growth can be represented by the amount of accumulated nitrite determined with the diazotization method (Hanson and Philips, *Method for general microbiology and molecular bacteriology*, 351-355, 1981). Following the diazotization method, the culture samples of *Symbiobacterium toebii* SC-1 were mixed with sulfanylamide solution and N-(1-naphthyl)-ethylenediamine dihydrochloride solution to develop color. After color development, the amount of accumulated nitrite is determined by measuring the absorbance of the mixture at 543 nm. The absorbance represents the relative growth of *Symbiobacterium toebii* SC-1 (see FIG. 4).

Figure 5:
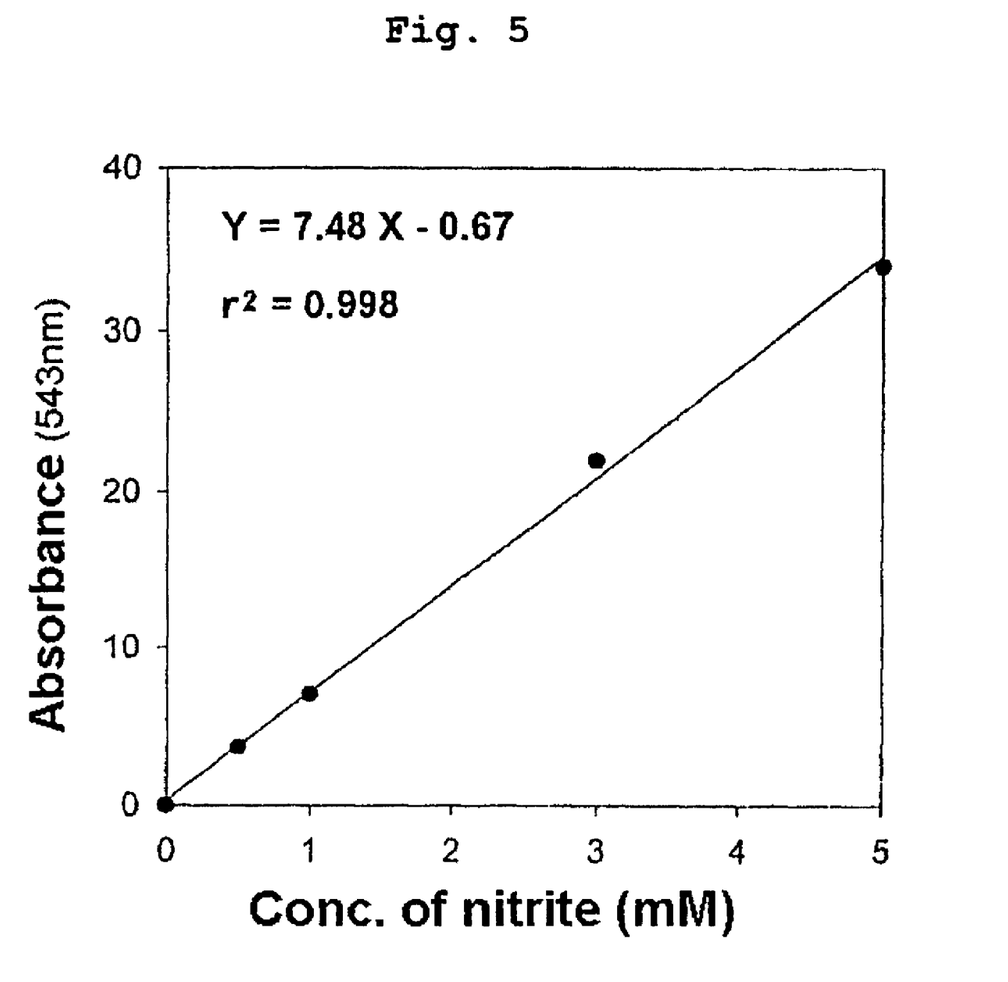
FIG. 5 shows an absorbance standard curve of nitrite measured by the diazotization method.

According to the absorbance standard curve of nitrite (see FIG. 5), the optical density of nitrite accumulated in culture mixtures is 30, and this value corresponds to 4 mM of nitrite. At this point, 1 mM of accumulated nitrite corresponded to $2.5 \times 10^6$ cells/ml of cell growth. Therefore, 4 mM nitrite concentration represents $1 \times 10^7$ cells/ml cell growth of *Symbiobacterium toebii* SC-1 in culture samples.

In this way a screening method of its relative bacteria from the environment by using a specific antibody to *Symbiobacterium toebii* SC-1 was designed.

Particularly, for the purpose of isolating its relative bacteria, a specific antibody to *Symbiobacterium toebii* SC-1 obtained from rabbits can be used. By dissolving it in a saline solution, mixing with environmental samples, and incubating the mixture, microorganisms bound to a specific antibody are separated from the mixture. The microorganisms purified as described above were inoculated into the modified basal medium containing L-tyrosine for enrichment culture or isolation of relative symbiotic bacteria from the environment.

EXAMPLES

Practical and presently preferred embodiments of the present invention are illustrated as shown in the following examples.

However, it will be appreciated that those skilled in the art, on consideration of this disclosure, may make modifications and improvements within the spirit and scope of the present invention.

Example 1

Identification of *Symbiobacterium toebii* SC-1

<1-1> Search for Microorganisms Showing a Thermostable L-tyrosine Phenol-lyase Activity To initiate enrichment cultures for isolating L-tyrosine phenol-lyase-producing microorganisms, these inventors used a basal medium (BM). The BM contained 5 g of polypeptone, 1 g of yeast extract, 6 g of $K_2HPO_4$, 2 g of $KH_2PO_4$, 0.5 g of $MgSO_4 \cdot 7H_2O$, and 0.5 g of L-tyrosine per liter of deionized water.

Specifically, enrichment cultures were initiated by inoculating BM with 1% compost samples. The samples were collected from compost yards in Kongjoo, Korea. The cultures were performed in 500 ml Erlenmeyer flasks with 200 ml of BM at 60° C. in a gyratory shaker. After two weeks of incubation, phenol, as a product of tyrosine phenol-lyase, was detected in the culture broth by reacting it with 4-aminoantipyridine reagent. Two milliliters of the culture showing phenol-positive reaction were transferred to 200 ml of fresh BM three times. The phenol was fully accumulated after each transfer.

These inventors tried to isolate the L-tyrosine phenol-lyase-producing microorganisms by using an end point dilution technique. The most diluted tubes showing phenol-positive reaction were transferred three times using the process of end point dilution. After three transfers, two kinds of cells in the phenol-positive cultures were always observed.

As a result of the enrichment for finding L-tyrosine phenol-lyase-producing thermophiles in compost at 60° C., initially, these inventors selected a culture showing a phenol-positive reaction that was detected after one week of incubation with various composts. After successive transfers, the activity was still maintained. In order to isolate a pure culture, the enrichment broth was serially diluted in BM and incubated. The end point diluted culture showing tyrosine phenol-lyase activity always had two types of bacterial strains, *Symbiobacterium toebii* SC-1 and *Bacillus* sp. SK-1. However, only *Bacillus* sp. SK-1 appeared on the BM agar plates and had no tyrosine phenol-lyase activity. These inventors could not isolate strain SC-1 from the mixed cultures.

Figure 1:
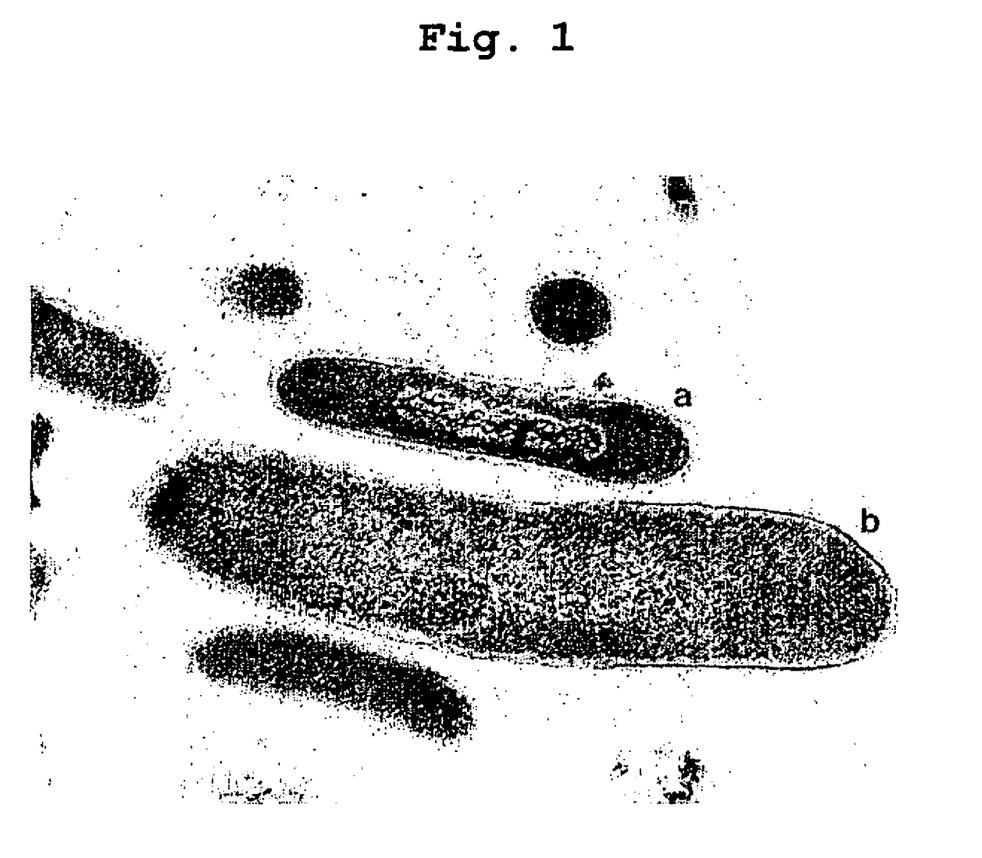
FIG. 1 shows an electron micrograph of a novel obligately symbiotic thermophile *Symbiobacterium toebii* SC-1 and its symbiotic partner *Bacillus* sp. SK-1.

However, these inventors confirmed that rod-shaped, Gram-negative microorganisms except *Bacillus* sp. SK-1, existed in the mixed cultures (FIG. 1).

<1-2> Isolation of *Symbiobacterium toebii* SC-1 from the Enrichment Culture

As a result of <1-1>, a single colony of *Bacillus* sp. SK-1 was isolated by spreading the enrichment cultures onto BM agar plates. However, no colony of the other strain, *Symbiobacterium toebii* SC-1, was detected on the BM agar plates. To isolate a single colony of *Symbiobacterium toebii* SC-1, these inventors used modified basal medium (MBM) containing the cell extract and culture supernatant of its symbiotic partner *Bacillus* sp. SK-1 and 10 mM nitrate. The culture supernatant was filter-sterilized and added to a 1:1 ratio by vol with BM. Cell extracts of centrifuged pellets were added after filter-sterilization. End point diluted cultures were spread onto the MBM agar plates and were incubated under an anoxic atmosphere. The colonies that appeared in MBM agar plates were transferred to new MBM plates. A single colony was transferred into liquid MBM in order to check purity and confirm its ability to produce L-tyrosine phenol-lyase. For maintenance, the pure culture was stored in a glycerol-MBM medium (50:50 by vol) mixture at −20° C.

Since no colony of strain SC-1 was detected on the plates of any nutrient media used, these inventors devised a modified medium basal medium to provide essential growth factors of symbiosis. When supernatants and cell extracts of pellets from the culture of its symbiotic partner *Bacillus* sp. SK-1 were supplemented to BM, micro-colonies (less than 0.1 mm in diameter) were detected on the MBM agar plates after 3 days incubation under anoxic conditions.

It was confirmed that these colonies were the novel symbiotic thermophiles producing L-tyrosine phenol-lyase because 4-aminoantipyrine reagent in their pure culture broth produced a red color.

<1-3> Characteristics of *Symbiobacterium toebii* SC-1

To determine the shapes and sizes of living and stained cells, these inventors used light microscopy. The Gram reaction was determined by light microscopy after cells were treated according to the method described by Bartholomew J. W., et al. (*Stain Technol.*, 37, 846-858, 1962). Physical contact between *Symbiobacterium toebii* SC-1 and *Bacillus* sp. SK-1 was monitored by light microscopy during cultures. For transmission electron microscopy, samples were fixed with glutaraldehyde and platinum-shadowed. Thin sections were obtained according to the method described by Miroshnichenko M. L., et al. (*Syst. Appl. Microbiol.*, 12, 257-262, 1989).

The colony of *Symbiobacterium toebii* SC-1 was translucent. *Symbiobacterium toebii* SC-1 is rod-shaped, gram-negative, 0.2 to 0.3 μm in diameter, and 1 to 5 μm long. Optimal temperature and pH for the growth of *Symbiobacterium toebii* SC-1 were about 60° C. and pH 7 to 8 (FIG. 2). These inventors detected colonies of *Symbiobacterium toebii* SC-1 on the MBM agar plates incubated under microaerobic conditions and nitrate reducing conditions. We confirmed that *Symbiobacterium toebii* SC-1 could grow in nitrate-reducing conditions in accordance with the accumulation of stoichiometric amounts of nitrite and no $N_2$ gas was produced. However, under aerobic conditions, growth of *Symbiobacterium toebii* SC-1 was severely restricted.

Major fatty acid compositions of *Symbiobacterium toebii* SC-1 are branched fatty acids and linear fatty acids, and major menaquinone compositions are MK-6 and MK-7.

Figure 3:
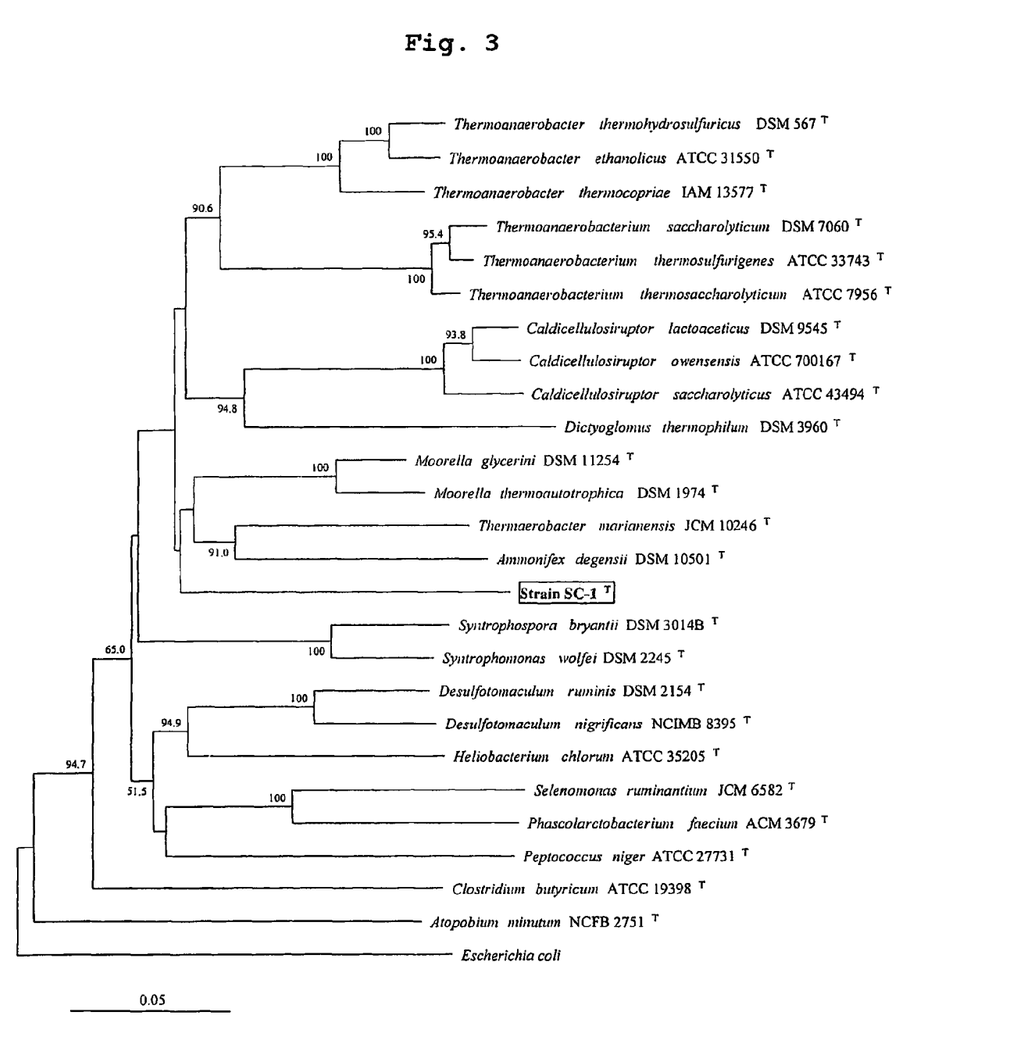
FIG. 3 shows a result of 16s rRNA nucleotide sequence analysis of the novel *Symbiobacterium toebii* SC-1.

As a result of phylogenetic analysis using 16s rRNA, it was confirmed that *Symbiobacterium toebii* SC-1 is a novel microorganism because it showed a similarity below 90% with previously defined bacterial groups (FIG. 3).

On the bases of these results, these inventors designated the novel symbiotic thermophile producing thermostable L-tyrosine phenol-lyase and L-tryptophan indole-lyase as *Symbiobacterium toebii* SC-1, and deposited it in the Korean Collection for Type Cultures (KCTC) at Korea Research Institute of Bioscience and Biotechnology (KRIBB) on Oct. 29, 1999 (Accession NO: KCTC 0685BP).

Example 2

Measurement of Thermostable L-tyrosine Phenol-lyase and L-tryptophan Indole-lyase Activities In order to measure enzyme activities of the thermostable L-tyrosine phenol-lyase and L-tryptophan indole-lyase produced by the identified novel symbiotic thermophile *Symbiobacterium toebii* SC-1 in this invention, these inventors prepared a crude cell extract. Particularly, *Symbiobacterium toebii* SC-1 was inoculated into liquid MBM, incubated under anoxic conditions with nitrate. The culture medium was then centrifuged to separate the cells. After that, a crude cell extract was obtained by sonicating the above cell pellets. Thermostable L-tyrosine phenol-lyase and L-tryptophan indole-lyase activity produced by *Symbiobacterium toebii* SC-1 were measured using this crude cell extract.

<2-1> Thermostable L-tyrosine Phenol-lyase Activity

To measure the enzyme activity of the thermostable L-tyrosine phenol-lyase produced by *Symbiobacterium toebii* SC-1, these inventors prepared an reaction mixture containing the crude extract sample with 0.2 ml of 0.1 M Tris-HCl buffer (pH 8.5) and 10 mM L-tyrosine. The reaction mixture was incubated at 60° C. for 1 hr. Pyruvate was produced as the result of the enzyme reaction. 0.2 ml of 60% potassium oxide salt solution and 0.1 ml of 2% salicylaldehyde were added to the enzyme reaction mixture, and the mixture was incubated at 37° C. for 30 min to develop the color. Following that, the mixture was diluted two-fold with a saline solution, and the enzyme activity was measured by determining the amount of pyruvate in the mixture.

As the result, the enzyme activity of tyrosine phenol-lyase was found to be 0.01 units/mg protein (Table 1).

<2-2> Thermostable L-tryptophan Indole-lyase Activity

To measure the enzyme activity of the thermostable L-tryptophan indole-lyase produced by *Symbiobacterium toebii* SC-1, these inventors prepared an enzyme reaction mixture that contained the crude extract with 0.2 ml of 0.1 M phosphate buffer and 10 mM L-tryptophan. The following steps are the same as in <2-1>.

As a result, the enzyme activity of L-tryptophan indole-lyase was found to be 0.34 units/mg protein (Table 1).

TABLE 1

Measurement of the thermostable L-tyrosine phenol-lyase and L-tryptophan indole-lyase activities

| | |
|---|---|
| Thermostable L-tyrosine phenol-lyase activity (units/mg proteins) | 0.01 |
| Thermostable L-tryptophan indole-lyase activity (units/mg proteins) | 0.34 |

* 1 unit of enzyme activity was defined as the amount of enzyme that could produce 1 μmol enzyme product in 1 min. The protein concentration was determined by the Bradford method.

As illustrated in Table 1, it was confirmed that the novel symbiotic thermophile *Symbiobacterium toebii* SC-1 in this invention produced the thermostable L-tyrosine phenol-lyase and L-tryptophan indole-lyase and these enzymes had activities producing pyruvate from L-tyrosine or L-tryptophan, respectively.

Therefore, the thermostable L-tyrosine phenol-lyase and L-tryptophan indole-lyase produced by *Symbiobacterium toebii* SC-1 in this invention were proved to be very stable biocatalysts in an enzymatic biotransformation process that synthesized L-DOPA from catechol, pyruvate and ammonia, or L-tryptophan from indole, pyruvate and ammonia.

Example 3

Growth Measurement of *Symbiobacterium toebii* SC-1 by Determining Nitrite Produced from Nitrate Respiration Since *Symbiobacterium* sp. strains were bacteria showing a very low growth yield, it was impossible to represent their growth by measuring their absorbances at $OD_{600}$ using spectrophotometer but also by counting number of microcolonies.

We used nitrate respiration under anaerobic conditions to determine the growth of *Symbiobacterium toebii* SC-1. It was confirmed that *Symbiobacterium toebii* SC-1 performed nitrate respiration under anaerobic growth conditions. Besides oxygen, *Symbiobacterium toebii* SC-1 used nitrate as an electron acceptor and reduced nitrate into nitrite. It also produced ATP using redox potential generated from nitrate respiration and used ATP for its growth.

Figure 4:
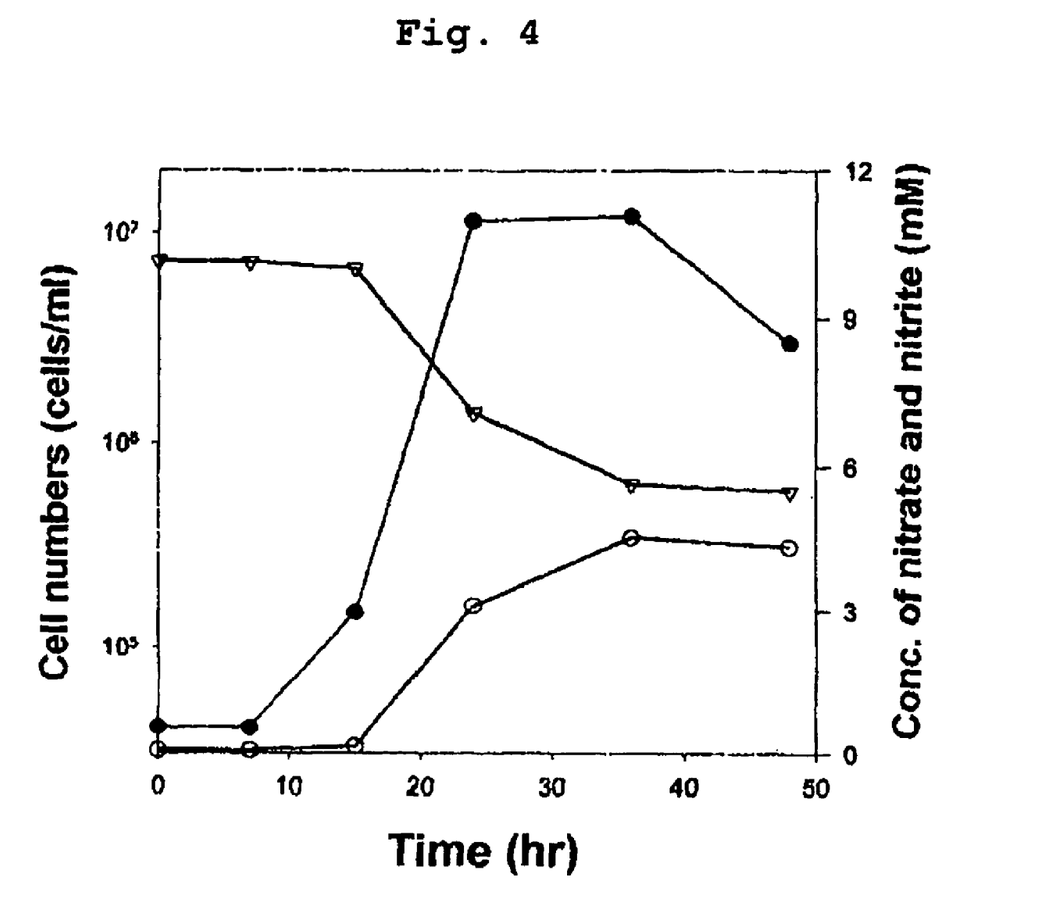
FIG. 4 shows the growth pattern of the novel *Symbiobacterium toebii* SC-1 which is cultivated by the pure culture method under nitrate reducing conditions, where -●-: the growth of *Symbiobacterium toebii* SC-1.

As described above, because the growth of *Symbiobacterium toebii* SC-1 using nitrate reduction coincides with accumulation of nitrite, its growth could be determined by measuring the amount of accumulated nitrite in the culture medium using the diazotization method (Hanson and Philips, *Method for general microbiology and molecular bacteriology*, 351-355). According to this method, these inventors mixed culture supernatants of *Symbiobacterium toebii* SC-1 with sulfanylamide solution and N-(1-naphthyl)-ethylenediamine dihydrochloride solution to develop a color. After color formation, the amount of accumulated nitrite was determined by measuring absorbance of the culture mixture at 543 nm and the measured absorbance represented a relative growth of *Symbiobacterium toebii* SC-1 (FIG. 4).

These inventors prepared an absorbance standard curve of nitrite (FIG. 5), and determined nitrite accumulated in the culture sample by this standard curve. We calculated a cell growth of *Symbiobacterium toebii* SC-1 from the determination of nitrite.

Figure 6:
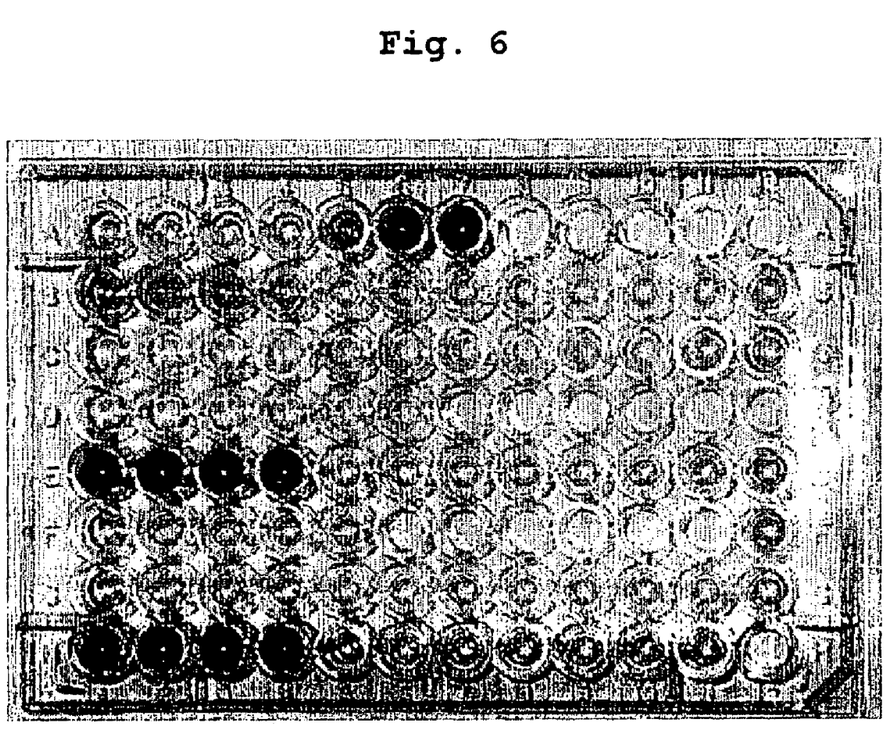
FIG. 6 shows low-growth measurement of *Symbiobacterium toebii* SC-1 using multi-well plates in which color intensity indirectly correlates with the growth of the cells.

At this point, 1 mM of accumulated nitrite corresponded to $2.5 \times 10^6$ cells/ml of cell growth. Consequently, absorbance (optical density, OD) of nitrite accumulated in culture samples was measured at 30, and this value represented a 4 mM nitrite concentration calculated with the standard curve (FIG. 4). Therefore, cell growth of *Symbiobacterium toebii* SC-1 in culture samples was $1\times10^7$ cells/ml. In addition, these inventors applied the above growth measurement method to multi-well plates and indirectly confirmed the growth of *Symbiobacterium toebii* SC-1 (FIG. 6).

Therefore, the growth measurement in this invention could be useful to determine not only the growth of *Symbiobacterium* sp. and its relative strains quickly and easily but it could also be used with environmental microorganisms showing low-growth yield whose growth has been impossible to represent up to now by using spectrophotometers or micro-colony counting.

Example 4

Screening of Its Relative Symbiotic Bacteria Using Specific Antibody to *Symbiobacterium toebii* SC-1

To isolate relative symbiotic bacteria of *Symbiobacterium toebii* SC-1 from the environment, the present inventors prepared a specific antibody to *Symbiobacterium toebii* SC-1. Particularly, the specific antibody to *Symbiobacterium toebii* SC-1 was prepared as follows. First, pure-cultured *Symbiobacterium toebii* SC-1 was treated with 0.5% formalin to fix. Next, the fixed *Symbiobacterium toebii* SC-1 was diluted with a saline solution. Finally, the diluted *Symbiobacterium toebii* SC-1 solution was inoculated into rabbits. Anti-serums recovered from rabbits were used as the specific antibody to *Symbiobacterium toebii* SC-1.

1 g of each environmental sample (composts, soil and hot spring water etc.) was diluted with 10 ml of 0.85% saline solution, and homogenized with an homogenizer. Then the mixture was centrifuged for 5 min (1,500 rpm) to separate the supernatant. 5 ml of the supernatant was mixed with 1 ml of the prepared specific antibody to *Symbiobacterium toebii* SC-1 and incubated at ambient temperature for 1 hr.

To separate microorganisms binding to a specific antibody in the mixture, the mixture was treated with 0.5 g of Protein A Sepharose (Pharmacia) which specifically bound to the antibody, and incubated at ambient temperature for 10 min. After that, microorganisms binding to the specific antibody complexes which interacted with Protein A Sepharose was separated by centrifugation and gently washed with a saline solution 3 times. Microorganisms isolated by the above method could be used for inocula of enrichment culture or for separating the symbiotic microorganisms after removing bound antibody-Protein A Sepharose complex by vortexing.

Therefore, the screening method of this invention could be useful to search for symbiotic microorganisms and separate them from the environment for investigation of microbial communities.

INDUSTRIAL APPLICABILITY

The present invention relates to a novel obligately symbiotic thermophile, *Symbiobacterium toebii* SC-1 and enzymes, thermostable L-tyrosine phenol-lyase and L-tryptophan indole-lyase, produced by *Symbiobacterium toebii* SC-1 which is cultivated by a pure culture method without mixed culture of its symbiotic partner, *Bacillus* sp. SK-1.

Therefore, the thermostable L-tyrosine phenol-lyase and L-tryptophan indole-lyase produced by *Symbiobacterium toebii* SC-1 in this invention can provide more stable biocatalysts in enzymatic biotransformation processes which enzymatically produce valuable medico-amino acids 3,4-dehydroxy-L-phenylalanine (L-DOPA) and L-tryptophan.

In addition, the present invention relates to a method of growth measurement for *Symbiobacterium toebii* SC-1 showing low-growth yield and a method for screening its relative symbiotic bacteria using specific antibody to the *Symbiobacterium toebii* SC-1.

It was demonstrated that the method of growth measurement in this invention can be useful to determine environmental microorganisms showing low-growth yield and that up till now it has been impossible to represent their growth using spectrophotometers or micro-colony counting. In addition, the screening method in this invention can be effectively used to search for symbiotic microorganisms and separate them from the environment for investigation of microbial communities.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An obligately symbiotic thermophile *Symbiobacterium toebii* SC-1 obtained by culturing *Symbiobacterium toebii* SC-1 in basal medium (BM) under anaerobic conditions, wherein the basal medium is modified to contain cell extract and culture supernatant of its symbiotic partner *Bacillus* sp. SK-1, and nitrate, and wherein the cell extract is prepared by sonication of *Bacillus* sp. SK-1.

2. The obligately symbiotic thermophile *Symbiobacterium toebii* SC-1 according to claim 1, wherein the basal medium contains polypeptone, yeast extract, $K_2HPO_4$, $KH_2PO_4$, $MgSO_4 \cdot 7H_2O$, and L-tyrosine.

3. The obligately symbiotic thermophile *Symbiobacterium toebii* SC-1 according to claim 2, wherein the nitrate is maintained at a concentration of 4 mM.

4. An obligately symbiotic thermophile *Symbiobacterium toebii* SC-1 (Accession NO: KCTC 0685BP).

\* \* \* \* \*